United States Patent

Kaska et al.

[11] Patent Number: 5,780,701
[45] Date of Patent: Jul. 14, 1998

[54] PROCESS FOR ALKANE GROUP DEHYDROGENATION WITH ORGANOMETALLIC CATALYST

[75] Inventors: William C. Kaska, Goleta, Calif.; Craig M. Jensen, Kailua, Hi.

[73] Assignees: The Regents of the University of California, Oakland, Calif.; University of Hawaii, Honolulu, Hi.

[21] Appl. No.: 687,717

[22] Filed: Jul. 26, 1996

[51] Int. Cl.[6] .......................... C07C 5/327; C07C 5/373; C07C 5/333; C07F 15/02
[52] U.S. Cl. .................. 585/654; 585/660; 556/13; 556/14; 556/21; 556/22; 556/23; 556/136; 556/137; 556/138; 556/140
[58] Field of Search ................ 585/659, 660; 556/14, 23, 138, 140, 13, 21, 22, 136, 137

[56] References Cited

U.S. PATENT DOCUMENTS

| | | | |
|---|---|---|---|
| 4,447,665 | 5/1984 | Wennerberg | 585/379 |
| 4,472,517 | 9/1984 | Tsao et al. | 502/62 |
| 4,473,505 | 9/1984 | Mitchell, III | 260/439 |
| 4,522,932 | 6/1985 | Mitchell, III | 502/153 |
| 4,950,798 | 8/1990 | Stobart et al. | 568/454 |
| 4,962,265 | 10/1990 | De Clippeleir et al. | 585/660 |
| 5,554,778 | 9/1996 | Beatty et al. | 556/21 |
| 5,559,262 | 9/1996 | Beatty et al. | 556/21 |
| 5,599,962 | 2/1997 | Beatty et al. | 556/21 |
| 5,689,003 | 11/1997 | Beatty et al. | 556/136 |

OTHER PUBLICATIONS

P. Clark. J. Organomet. Chem., vol. 110, pp. C13–C15, Apr. 1976.

(List continued on next page.)

*Primary Examiner*—Glenn Caldarola
*Assistant Examiner*—J. Pasterczyk
*Attorney, Agent, or Firm*—Peters, Verny, Jones & Biksa L.L.P.

[57] ABSTRACT

An improved process is described for the catalytic dehydrogenation of organic molecules having a

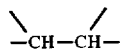

group to produce a

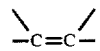

group. The organic molecules are:

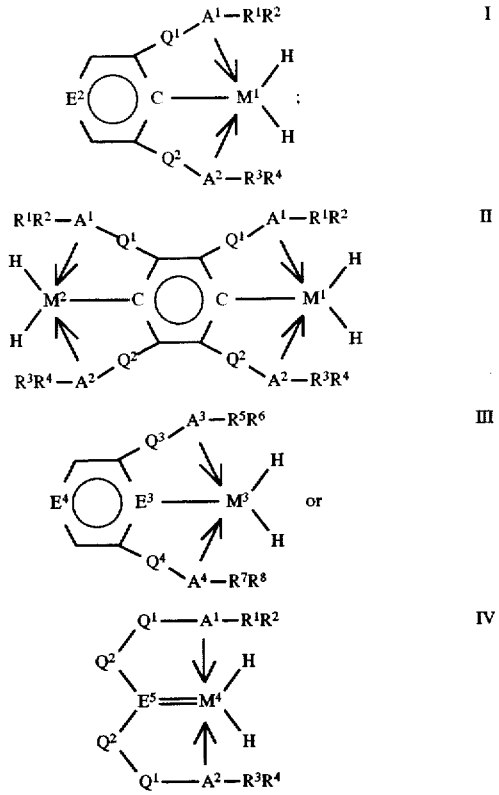

wherein:

$A^1$, $A^2$, $A^3$, and $A^4$ are each independently P, As or N; $E^2$ is independently C or N; $E^3$ is independently C, Si or Ge; $E^4$ is independently C, Si, or Ge; and $E^5$ is independently C, Si or Ge; $M^1$, $M^2$, $M^3$, and $M^4$ each is a metal atom independently selected from the group consisting of ruthenium, rhodium, palladium, osmium, iridium and platinum; $Q^1$, $Q^2$, $Q^3$, and $Q^4$ are each independently a direct bond, $-CH_2-$, $-CH_2CH_2-$, or $CH=CH-$;

in structure I, structure II or structure IV, $R^1$, $R^2$, $R^3$, and $R^4$ are each independently selected from alkyl, alkenyl, cycloalkyl, and aryl, or $R^1$ and $R^2$ together and $R^3$ and $R^4$ together form a ring structure having from 4 to 10 carbon atoms, or in structure III, $R^5$, $R^6$, $R^7$, and $R^8$ are each independently selected from alkyl, alkenyl, cycloalkyl, and aryl, or $R^5$ and $R^6$ together and $R^7$ and $R^8$ together form a ring structure having from 4 to 10 carbon atoms, at a temperature of between about 100° and 250° C. for between about 1 hr and 300 days in the absence of $N_2$. The surprisingly stable catalyst is a complex of an organic ligand comprising H, C, Si, N, P atoms, and a platinum group metal. The dehydrogenation is performed between about 100 to 200° C., and has increased turnover.

20 Claims, No Drawings

OTHER PUBLICATIONS

P. Clark. J. Organomet. Chem., vol. 137, pp. 235–255, Sep. 1977.

M. Gupta et al., Chem. Commun., 1996, pp. 2083–2084, Sep. 1996.

C.J. Moulton, et al., *J.C.S. Dalton* pp. 1020–1024 (1975).

S. Nemeh, et al., *Organometallics 2*, pp. 1442–1447 (1983).

D. Baudry, et al., *J. Chem. Soc., Chem. Commun.* pp. 788–789 (1983).

H. Felkin, et al., *Tetrahedron Letters 26* (16), pp. 1999–2000 (1985).

H. Felkin, et al., *Tetrahedron Letters 25* (12), pp. 1279–1282 (1984).

M. Burk, et al., *J. Chem. Soc., Chem. Commun.* pp. 1829–1830 (1985).

M. Burk, et al., *J. Am. Chem. Chem. Soc. 109* pp. 8025–8032 (1987).

K. Nomura, et al., *J. Chem. Soc., Chem. Commun.* pp. 161–162 (1988).

J. Maguire, et al., *J. Am. Chem. Soc. 111* pp. 7088–7093 (1989).

K. Nomura, et al., *J. Mol. Catalysis 54* pp. 57–64 (1989).

T. Sakakura, et al., *New J. Chem.* pp. 737–745 (1989).

T. Fujii, et al., *J. Chem. Soc., Chem. Commun.* pp. 757–758 (1990).

T. Sakakura, et al., *Chem. Letters* pp. 297–298 (1991).

J. Maguire, et al., *J. Am. Chem. Soc. 113* pp. 6706–6708 (1991).

J. Maguire, et al., *J. Am. Chem. Soc. 114* pp. 9492–9498 (1992).

T. Aoki, et al., *Organometallics 12* pp. 294–298 (1993).

M. Fryzuk, *Can. J. Chem. 70* pp. 2839–2845 (1992).

T. Fujii, *J. Chem. Soc. Dalton Trans.* pp. 517–520 (1993).

M. McLoughlin, et al., *Organometallics, 13* (10) pp. 3816–3822 (1994).

J. Perry et al., *Organometallics, 13* pp. 1870–1877 (1994).

R. A. Gossage, et al., *Inorg. Chem. 35* pp. 1729–1732 (1996).

K. Wang, et al., *J. Organometallic Chem. 518* pp. 55–68 (1996).

J. A. Miller, et al., *J. Chem. Soc., Chem. Commun.* pp. 1449–1450 (1994).

PROCESS FOR ALKANE GROUP DEHYDROGENATION WITH ORGANOMETALLIC CATALYST

ORIGIN OF THE INVENTION

This invention was completed with funding in part from the U.S. Department of Energy (Hydrogen Program), Contract No. DE-FC36-94AL85804. The U.S. Government has certain rights in this invention.

BACKGROUND OF THE INVENTION

1. Field of Invention

The present invention concerns an improved process to remove adjacent hydrogens in a

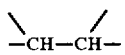

group in an organic compound to produce a

group. The hydrogen removal process using a family of organometallic complexes as described herein occurs at moderate and at high temperatures and at higher turnover rates than previously found. The catalyst is surprisingly stable at high temperatures.

2. Description of Related Art

Saturated hydrocarbons are among the most abundant components of petrochemicals and yet are generally unreactive in chemical reactions. Alkenes, however, are very useful as raw materials in the organic chemical industries. Thus, there has been much interest in processes which efficiently convert alkanes to alkenes.

A great deal of effort has been placed in developing stable compounds which assist in the dehydrogenation of an alkane containing structure to an alkene containing structure at high turnover rates. Soluble metal complexes have been found to catalyze the dehydrogenation of alkanes. But the reactions are normally endoergonic and need to include an external driving force. Systems have been previously developed which describe the use of photoirradiating, thermal evolution of hydrogen and hydrogen transfer from alkanes to hydrogen acceptors to drive the reaction. New metal complexes are being explored which maintain long catalytic activity under driving process conditions and which also create a high turnover rate for alkanes to alkenes.

Photoirradiation has been widely used to activate several metal complexes. One such compound is the Vaska-type complex, with the general formula RhCl(CO)(PR$_3$)$_2$, wherein PR$_3$ is PPh$_3$, PEtPh$_2$, PEt$_2$Ph, PEt$_3$ and PMe$_3$. K. Nomura, et al, *J. Chem Soc. Chem. Commun.* (1988), p. 161–162, and K. Nomura, et al, *J. Mol. Catal.* (1989), Vol. 54, p. 57–64 report that the reaction takes place by the reversible dissociation of carbon monoxide. According to Nomura, irradiation is necessary for reductive elimination of CO in these metal polyhydride complexes. In fact, no reaction takes place without photoirradiation. Variations of the Vaska-type complex, such as RhCl(CH$_2$=CH$_2$)(PMe$_3$)$_2$, also were found to require irradiation with visual light in order to initiate the reaction. See, for example, T. Sakakura, et al. *Chem. Lett.* (1991), p. 297–298. The turnover rate was high in these systems, for example, 300 turnovers/hour for cyclooctane in J.A. Maguire, et al, *J. Am. Chem. Soc* (1989), Vol. 111, p. 7088–7093. A major disadvantage of these irradiation dependent systems is that the catalyst was short lived. See, for example, T. Sakakura, et al., *New J. Chem.* (1989), Vol. 13, p. 737–745, wherein the metal complex was highly productive for only 48 hours at 96° C.

In order to avoid the need for irradiation steps, prior investigations sought to replace the need for photoirradiation with thermally driven reactions. In T. Fujii, et al, *J. Chem. Soc. Chem. Commun.* (1990), p. 757–758, and T. Aoki, et al., *Organometallics* (1993), Vol. 12, p. 294, the evolved hydrogen is separated from the catalyst and the gas phase in contact with the solution, causing the vapor phase to consist exclusively of solvent molecules. No irradiation is needed to drive the reaction because the refluxing condition was found to overcome the equilibrium restriction. The Wilkinson complex is used as the metal catalyst in these refluxing systems, having the general formula, RhClL$_3$, wherein L is (PPh$_3$), (PMePh$_2$) or P(C$_6$H$_4$Me-p)$_3$. It was found by T. Fujii, *J. Chem. Soc.* (1993), p. 517–520, that bromide may be substituted for chloride in the complex to increase rates of hydrogen evolution. Although thermal reactions circumvent the use of irradiation, the turnover rates are significantly lower at about 1.10 turnovers per hour (hr) for cyclooctanes. Furthermore, the problem encountered of a short catalytic life still persists to an even greater extent. The Wilkinson complex decreases its activity by about 75% after 24 hours.

Hydrogen transfer to hydrogen acceptors has been one of the most widely researched pathways with several types of soluble metal catalysts. Early description of hydrogen acceptors is in D. Baudry, *J. Chem. Soc. Chem. Commun.* (1983), p. 788–789, which includes the use of (Ar$_3$P)$_2$ReH$_7$, wherein Ar is p-F-C$_6$H$_4$, Ph or p-Me-C$_6$H$_4$. The catalyst in Baudry's system proved to be very low in reactivity and longevity, reaching a maximum turnover rate of 1.6 at 10 minutes. Other catalysts were tried in M.W. Burk, *J. Chem. Soc. Chem. Commun.* (1985), p. 1829–1830 such as IrH$_2$(CF$_3$CO$_2$)(Pcy)$_2$ wherein cy is cyclohexyl. But reactivity was consistently low, only 2 turnovers of cyclooctane. The activity increased to 34 turnovers but over two weeks as reported by M. W. Burk, *J. Am. Chem. Soc.* (1987), Vol. 109, p. 8024–8032 using IrH$_2$(n$^2$-O$_2$CCF$_3$(PR$_3$)$_2$-. Turnover rates remained in this low range also in H. Felkin, et al. *J. Tetrahedron Lett.* (1984), Vol. 25, p. 1279–1282 and H. Felkin, et al. *J. Tetrahedron Lett.* (1985), Vol. 26, p. 1999–2000 with the catalyst, (iPr$_3$P)$_2$IrH$_5$.

In J. A. Maguire, *J. Am. Chem. Soc.* (1991), Vol 113, p. 6706–6708, the Vaska-type complex is used as a catalyst without the necessity of irradiation by use of a hydrogen acceptor. It is speculated that the thermodynamic barrier to CO loss as described above is overcome by simultaneous alkene hydrogenation of the acceptor. J. A. Maguire was able to significantly improve turnover rates (see *J. Am. Chem. Soc.* (1992) Vol. 114, No. 24, pp 9492–9498), but only under high hydrogen pressure, and the reaction requires sacrificial hydrogenation of 4–20 fold excess of an acceptor alkene in conjunction with the alkane dehydrogenation.

The following patents and references are also of interest:

A. N. Wennerberg in U.S. Pat. No. 4,447,665, discloses a method for dehydrogenating a paraffinic or naphthionic compound at about 465° to 650° C. using an active carbon catalyst having a cage-like structure and a BET surface area of at least 800 square meters per gram having a uniform dispersion of a metal.

Y-Y. P. Tsai, et al. in U.S. Pat. No. 4,472,517 disclose the preparation of metal-containing zeolite catalysts having increased stability and activity, which catalysts are useful in dehydrogenation.

U.S. Pat. No. 4,473,505 discloses phosphine and phosphonium compounds and catalysts which are useful in dehydrogenation. The ligands include P—C—S atoms, and contain a —C≡C— bond, which combines with a transition metal such as platinum or nickel.

H. L. Mitchell in U.S. Pat. No. 4,552,932 discloses ligand materials and transition metal complexes useful in catalytic dehydrogenation. Ligands containing M—O—L linkages are disclosed wherein M is Si or Ti and L is P or As.

S. R. Stobart et al. in U.S. Pat. No. 4,950,798 disclose a catalytic process for hydroformylation. The catalyst is a chelate of a platinum-group metal and a P—Si—C ligand.

G. E. M. M. De Clippeleir et al. in U.S. Pat. No. 4,962,265 disclose process and a catalyst for the catalytic dehydrogenation of hydrocarbons. The catalyst is a platinum-metal group metal being deposited into an alumina support.

S. Nemeh, et al., Organometallics (1993), vol. 2, pp. 1442–1447, describe interaction of (2,6-bis((di-tert-butylphosphine)methyl)phenyl) methyl rhodium I, and similar structures with hydrocarbons, i.e.:

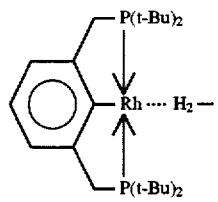

R. A. Gossage, et al. in Inorganic Chemistry (1996) vol. 35, pp. 1729–1732 disclose some (phosphenoalkyl) silanes.

M. A. McLoughlin, et al., Organometallics (1994), vol. 13, pp. 3816–3822 describe a family of complexes of ligands of P and C with iridium metal.

M. D. Fryzuk in the *Canadian Journal of Chemistry* (1992), Vol. 70, p. 2840–2845, discloses the design of ligands useful for coordination of ligands to bind metal atoms.

However, a strong need still exists for a family of novel organometallic catalytic compounds (complexes) which maintain integrity over a long reaction time at moderate reaction temperatures and create a high turnover rate in dehydrogenation of alkane to alkene.

All of the disclosures in the references, patents, standards, etc. cited herein are incorporated herein by reference.

These references do not teach or suggest a process for dehydrogenating alkane containing structures to alkene containing structures, including long term maintenance of catalyst integrity at elevated temperatures and with high turnover rates as is described in the present invention. In particular, they do not teach or suggest a process whereby ethylbenzene can be dehydrogenated to produce styrene at moderate (at less than 600° C.) temperatures.

SUMMARY OF THE INVENTION

The present invention concerns an improved process to remove hydrogen from an alkyl-containing compound having at least one —CH—CH— group to produce an alkane-containing compound having at least one —C=C— bond, which process comprises:

(a) contacting the alkyl-containing organic compound with a soluble organometallic complex of structure A, which structure is selected from structures I, II, III or IV:

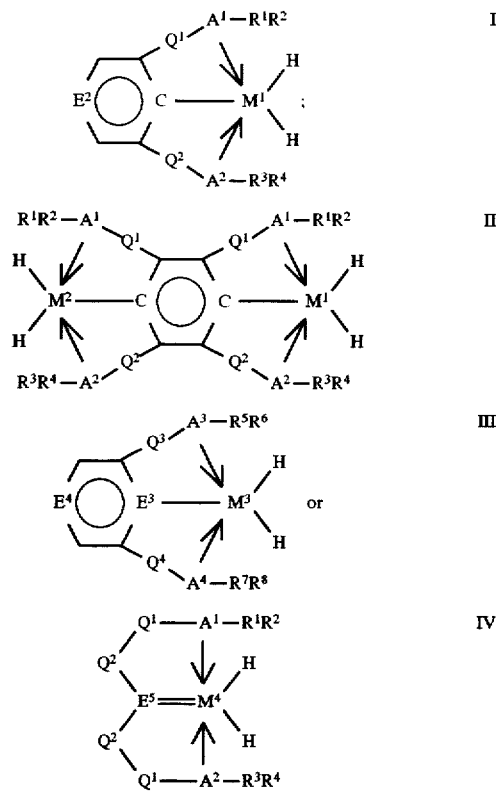

wherein:
$A^1, A^2, A^3$ and $A^4$ are each independently selected from P, As, or N;
$E^2$ is independently selected from C or N;
$E^3$ is independently selected from C, Si, or Ge;
$E^4$ is independently selected from C, Si, or Ge;
and $E^5$ is independently selected from C, Si or Ge.
$M^1, M^2, M^3$ and $M^4$ are each a metal atom selected from the platinum metal; group of ruthenium, rhodium, palladium, osmium, iridium and platinum.
$Q^1, Q^2, Q^3$ and $Q^4$ are each independently selected from a direct bond, —$CH_2$—, —$CH_2CH_2$— or —CH=CH—;
in structure I or structure II, $R^1, R^2, R^3$ and $R^4$ are each independently selected from alkyl, alkenyl, cycloalkyl, aryl, substituted aryl, or $R^1$ and $R^2$ together and $R^3$ and $R^4$ together form a ring structure having from 4 to 10 carbon atoms, or
in structure III, $R^5, R^6, R^7$ and $R^8$ are each independently selected from alkyl, alkenyl, cycloalkyl, aryl, substituted aryl, or $R^5$ and $R^6$ together and $R^7$ and $R^8$ together form a ring structure having from 4 to 10 carbon atoms;
at a temperature of between about 100° and 250° C. for between about 1 hr and 300 days in the absence of nitrogen.

The present invention also concerns an improved process to remove hydrogen from an alkyl-containing compound having at least one

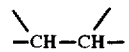

group to produce a corresponding alkene-containing compound having at least one

group, which process comprises:
(a) contacting the alkyl-containing compound from which nitrogen has been removed with a soluble organometallic complex of structure A, which structure A is selected from structure I:

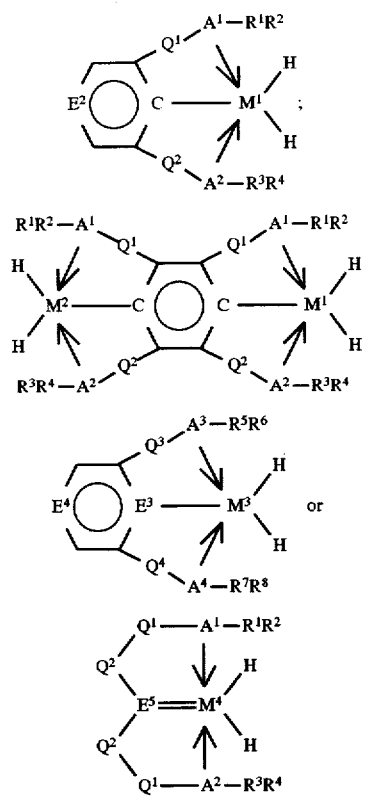

wherein:
$A^1, A^2, A^3$ and $A^4$ are each independently selected from P, As or N;
$E^2$ is independently selected from C or N;
$E^3$ is independently selected from C, Si, or Ge;
$E^4$ is independently selected from C, Si, or Ge;
and $E^5$ is independently selected from C, Si or Ge.
$M^1, M^2, M^3,$ and $M^4$ are each a metal atom selected from the platinum metal group;
$Q^1, Q^2, Q^3$ and $Q^4$ are each independently selected from a direct bond, $—CH_2—$, $—CH_2CH_2—$ or $—CH=CH—$,
in structure I or structure II, $R^1, R^2, R^3$ and $R^4$ are each independently selected from alkyl, alkenyl, cycloalkyl, aryl, substituted aryl, or $R^1$ and $R^2$ together and $R^3$ and $R^4$ together form a ring structure having from 4 to 10 carbon atoms, or
in structure III, $R^5, R^6, R^7$ and $R^8$ are each independently selected from alkyl, alkenyl, cycloalkyl, aryl, substituted aryl, or $R^5$ and $R^6$ together and $R^7$ and $R^8$ together form a ring structure having from 4 to 10 carbon atoms;
at a temperature of between about 100° and 250° C. for between about 1 hr and 360 days in the absence of nitrogen; and optionally
(b) the alkene-containing compound, hydrogen or combinations thereof of step (a) is recovered.

Preferably, the temperature of the dehydrogenation is between about 150° and 250° C., more preferably between about 150° and 200° C.

Preferably, the time of the dehydrogenation is between about 0.5 hour and 100 days, more preferably between about 1 hour and 30 days. Useful times include for example, 0.5 hour, 1 hour, 5 hours, 1 day, 5 days, 7 days, and 30 days.

DETAILED DESCRIPTION OF THE INVENTION AND PREFERRED EMBODIMENTS

Definitions

As used herein:

"Aliphatic group", "alicyclic group" refer to any linear, branched, cyclic, or bridged hydrocarbon having a configuration which will produce a reactive organometallic complex.

Examples include the structures in the claims and also the following structure:

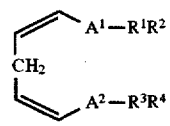

wherein $A^1, A^2, R^1, R^2, R^3, R^4,$ and M are defined above.
"Alkyl-containing compound" refers to any organic compound to be dehydrogenated. This compound has at least one $—CH—CH—$ group which is converted to a $—C=C—$ bond by the present process. Thus, an alkyl-containing compound includes, but is not limited to, alkanes cycloalkanes, bicycloalkanes, fused alkanes, alkylaryenes, and the like. Alkanes include, but are not limited to, the linear, branched or cyclic compounds; ethane, propane, butane, pentane, hexane, heptane, octane, and the like up to alkanes having 20 carbon atoms. Alkyl benzenes include, for example, ethyl benzene, propyl benzene, p-diethylbenzene and the like. These organic compounds also may contain unsaturation and/or heteroatoms such as Si, N, P, etc.

"Aromatic group" refers to any conventional ring structure which has a configuration and substituents which produce a reactive organometallic complex. Examples include the structures in the claims and also the following structures:

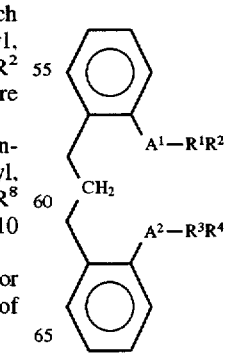

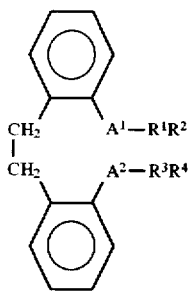

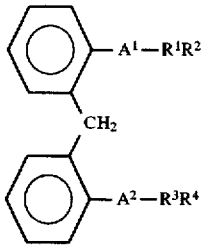

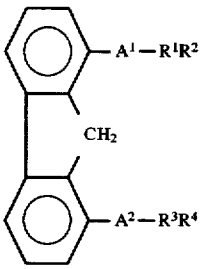

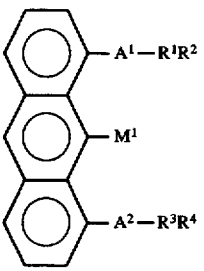

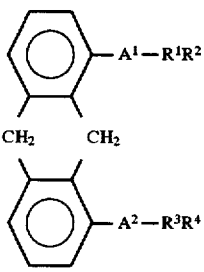

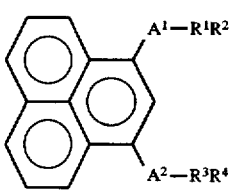

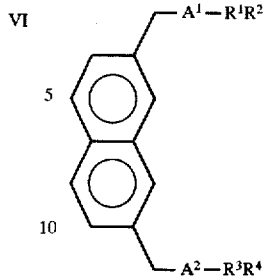

VI wherein $A^1$, $A^2$, $R^1$, $R^2$, $R^3$, $R^4$, and $M^1$ are defined above.

"Platinum group metal" refers to those elements designated as platinum group of the conventional periodic table. These include, Fe, Ru Os, Co, Rh, Ir, Ni, Pd, and Pt. Rh, Ir and Pt are preferred.

"THF" refers to the conventional solvent tetrahydrofuran.

"Heteroaliphatic group" refers to any linear, branched, alicyclic, carbocyclic or bridged hydrocarbon wherein at least one of the carbons has been replaced by: Si, S, Sn. Examples include the structures in the claims and include the following structure:

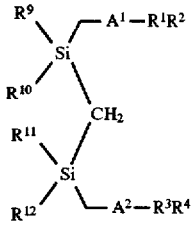

VIII wherein $A^1$ and $A^2$, $R^1$, $R^2$, $R^3$, $R^4$, and M are defined above, and $R^9$, $R^{10}$, $R^{11}$ and $R^{12}$ are alkyl.

IX

"Heteroaromatic group" refers to any conventional ring structure having one or more of the carbons in the aromatic ring substituted by P, N, or combinations thereof. Examples include the structures in the claims of the following structures:

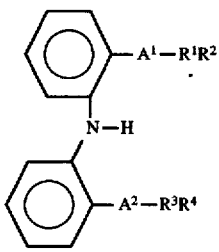

XIV

X

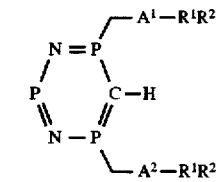

XI

"Turnover" refers to the number of moles of product formed per mole of catalyst. It is an art accepted measure for catalyst activity. The number of turnovers/hr is surprisingly high. Preferably, the number of turnovers at 150° C. is between about 50 and 2000 hours, more preferably between 50 and 1000 hours. Preferably, the number of turnovers at 200° C. is between about 500 and 5000 hours, more preferably between about 1000 and 5000 hours.

Description:

The improved method to obtain dehydrogenation of an alkyl containing group uses a complex of a ligand and a platinum group metal. The ligand is an organic molecule which may also contain P, N, or Si. The complex permits improved selectivity and improved activity (increase in turnover) in the dehydrogenation of alkyl-containing compounds when performed at 100° to 200° C.

The present process and catalyst are useful in the production of alkylenes, in the production of hydrogen, and in the production of aromatic organic compounds. It is also useful for hydrocarbon reforming.

Specific dehydrogenations have been performed using Complex IA and IIB which correspond to Structure I in the summary.

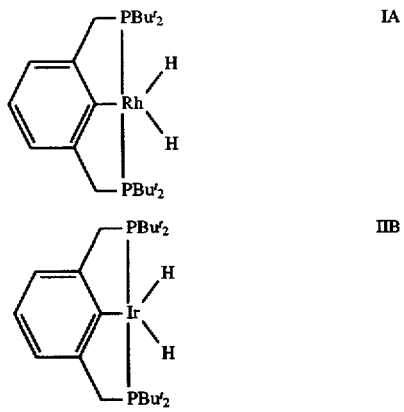

It is to be understood that any of the groups of these structures may be replaced by the structures II, III or IV described in the Summary for Structure I and a corresponding dehydrogenation will be achieved.

The complexes $RhH_2(C_6H_3-2,6-(CH_2PBu^t{}_2)_2)$ (IA) and $IrH_2(C_6H_3-2,6(CH_2PBu^t{}_2)_2$ (IIB) were prepared in greater than >85% to yield by treatment of the corresponding hydrido chloride complexes (C. J. Moulton, et al. (1976)) with a THF solution of $LiBEt_3H$ at 25° C. under an atmosphere of $H_2$ as shown in equation 1.

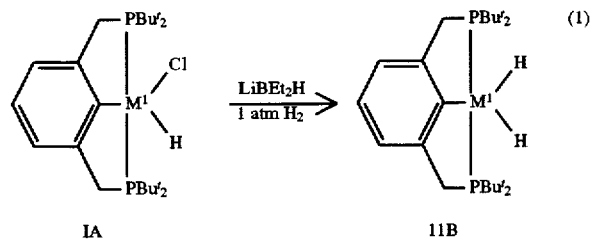

The solutions containing Complex IIA show no signs of catalyst decomposition up to one week of reaction time at all temperatures studied (150°–200° C.), and the solutions remain active to the limit of complete hydrogenation of the hydrogen acceptor. The reaction is unaffected by the addition of metallic mercury to the mixture indicating that metallic iridium is not involved in the hydrogen transfer (D. R. Anton et al. (1982)). Comparable high levels of catalytic activity have previously been achieved only in systems catalyzed by $RhCl (PMe_3)_2(CO)$ which require the sacrificial hydrogenation of 6 to 8 equivalents of norborene and 68 atm of hydrogen (J. A. Maguire et al. (1991)(1992)). Far greater activity with Complex IIA than Complex IA is in accordance with a recent theoretical study by Goddard et al. (Perry et al., Orgonometallics (1994), Vol. 13, p. 1870-1877, which identified Ir+ as the most efficient transition metal for the dehydrogenation of methane. The differences in the catalytic activities of Complex IA and Complex IIA are possibly related to the ability of iridium to form stronger M-C and M-H bonds and the availability of the Ir(V) oxidation state.

At high concentrations, both t-butylethylene (tbe) and the hydrogenated product, t-butylethane (tba) acts as an inhibitor of the catalytic reaction. Diminished rates of catalysis are found in solutions containing greater than a 300:1 ratio of t-butylethylene to catalyst. Thus, high turnover numbers are achieved only in solutions containing a limited amount of tbe which must be periodically added to the reaction mixture. The inhibition of the catalytic system by the product tba limits the attainable number of turnovers to about 1000. The catalytic activity is also strongly inhibited by nitrogen. In order to achieve the maximum catalytic rates, the solutions must be freeze-pump-thaw degassed prior to heating to remove any vestiges of nitrogen. Apparently, nitrogen coordination is competitive with alkane coordination. This result is supported by the recent finding of Milstien et al (Organometallics (1996) Vol. 15, p. 1839-1844) that $Rh(H_2)(HC(CH_2CH_2PBu^t{}_2)_2)$ is converted to $Rh(N_2)(CH_2CH_2PBu^t{}_2)_2)$ when placed under an atmosphere of nitrogen. The dehydrogenation is performed in the absence of nitrogen. Nitrogen is removed from the organic compound feed by a conventional freeze-pump-thaw degassing. Alternatively, the nitrogen is removed by purging the organic feed and system thoroughly with an inert gas, such as neon or argon.

Complex 1A was previously prepared in inferior yield by the reaction of the hydrido chloride complex with KH (S. Nemeh, et al. (1983)). The complexes were purified and isolated upon recrystallization from pentane.

Complex II catalyzes the transfer-dehydrogenation of cyclooctane at rates which are two orders of magnitude greater than those of previously reported catalytic systems which do not require the sacrificial hydrogenation of a large excess of hydrogen acceptor (J. A. Maguire, et al. (1991) (1993)). Furthermore, the P-C-P pincer complexes have unprecedented, long term stabilities under catalytic conditions and moderately elevated temperature.

Turnover in the present invention is increased significantly.

In conclusion, the surprising and unexpected aspect of the invention is that by using the process with the inventive stable catalyst, it is possible to perform the reaction at moderately elevated temperatures of between about 100°–200° C. having improved turnover times to increase the yield of the dehydrogenation reaction as compared to other similar dehydrogenations.

The following examples are provided to further explain and describe the invention. They are not to be construed to be limiting in any way.

GENERAL

Gas chromatography-Mass Spectroscopy (GC-MS) analysis was performed on a temperature programmed (35° C. isothermal for 3 min; 2°/min to 60° C.) Hewlett Packard 5890 gas chromatograph using 250 μm 25% m OV-1 capillary columns coupled to a VG 70SB dual sector high resolution mass spectrometer.

The $^1H$ and $^{31}P$ Nuclear Magnetic Resonance (NMR) spectra of IA obtained through this procedure were identical to those previously reported. (b) For IIA: $^1H$ NMR (400 MHz, toluene-$d_8$), delta 7.4 d, $J_{H-H}$=7.4 Hz, $^1H$, para aromatic; 7.2 br s, 2H, meta aromatic; 336, vt, $J_{P-H}$. $^{31}P(^1H)$ NMR (161.9 MHz, toluene-d$_8$), delta 90.4. Anal. Calcd: C, 49.04; H, 7.72. Found: C, 49.12 H, 8.21.

EXAMPLE 1

Dehydrogenation of Cyclooctane (a) Several solutions of cyclooctane (4.0 mL, 37.0 mmol) and the (0.2 mL, 1.6 mmol) were charged with Complex IA (10 mg, 0.019 mmol), in sealed tubes under argon, and fully immersed in an oil bath for the prescribed reaction times (e.g., ½hour, 1 hour, 5 hours, 5 days, 7 days, 30 days). The production of cyclooctene was quantified by gas chromatography. At 150° C., the reaction mixtures containing Complex IA did not darken or discolor during reaction periods as long as one week. The long term maintenance of catalyst integrity at 150° C. is in contrast to the short, about 12-hour half lives, generally found for other dehydrogenation catalysts at 150° C. The rate of catalysis is 0.8 turnovers/hr at 150° C. The rate increases to 1.8 turnovers/hr at 200° C.; however, significant decomposition of Complex IA is apparent after 24 hr.

(b) Similarly, when Example 1(a) is repeated except that cyclooctane is replaced with a stoichiometrically equivalent amount of n-hexane or cyclohexane, a corresponding dehydrogenation occurs producing 1-hexene, 2-hexene or benzene, respectively.

(c) Similarly, when Example 1(a) is repeated except that cyclooctane is replaced by a stoichiometrically equivalent amount of decalin, a corresponding yield of naphthalene is obtained.

EXAMPLE 2

Dehydrogenation of Cyclooctane (a) Strikingly higher activity is observed in solutions of cyclooctane (4.0 mL, 37.0 mmol), tbe (0.2 mL, 1.6 mmol), and the iridium Complex IIB (3 mg, 0.0051 mmol). At 150° C., the dehydrogenation of cyclooctane proceeds at the rate of 82 turnovers/hr while a rate of 716 turnovers/hr is observed at 200° C. Appreciable activity (20.5 turnovers/hr) is found even at a temperature 100° C.

(b) Similarly, when Example 2(a) is repeated except that cyclooctane is replaced with a stoichiometrically equivalent amount of n-hexane or cyclohexane, a corresponding dehydrogenation occurs producing 1-hexene, 2-hexene and benzene, respectively.

(c) Similarly, when Example 2(a) is repeated except that cyclooctane is replaced by a stoichiometrically equivalent amount of decalin, a corresponding yield of naphthalene is obtained.

(d) Similarly, when Example 2(a) is repeated except that in Complex IIB, Ir is replaced by ruthenium or platinum and a corresponding yield of cyclooctene is produced.

EXAMPLE 3

Dehydrogenation of Ethylbenzene (a) Solutions of ethylbenzene (4 mL, 32.7 mmol) and the 0.2 mL, 1.6 mmol) were charged with Complex IIB (3 mg, 0.0051 mmol). At 150° C., production of styrene proceeds at the rate of 14 turnovers/h while a rate of 79 turnovers/h is observed at 200° C.

(b) Similarly, when Example 3(a) is repeated except that in Complex IIB, the Ir is replaced by rhodium or ruthenium and a corresponding amount of styrene is produced.

(c) While only a few embodiments of the present invention have been shown and described herein, it is apparent to those skilled in the art that various modifications and changes can be made in these novel processes using a soluble organometallic complex to produce a 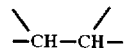 group from a —CH—CH— group in an organic compound without departing from the spirit and scope of the present invention. All such modifications and changes coming within the scope of the appended claims are intended to be covered thereby.

We claim:

1. An improved process to remove hydrogen from an allyl-containing organic compound having at least one

group to produce an alkene compound having at least one

group, and hydrogen which process comprises:

(a) contacting the alkyl-containing compound with a soluble complex of structure A, which structure is selected from structure I:

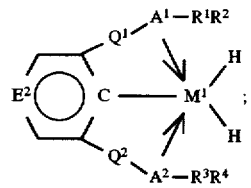

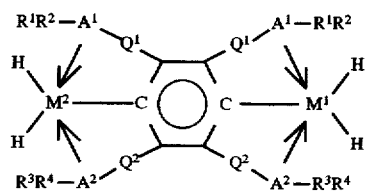

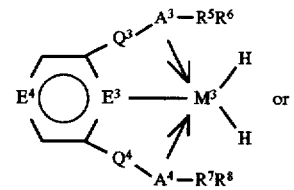

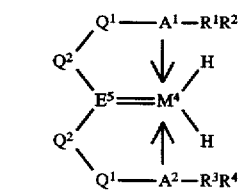

wherein:
$A^1$, $A^2$, $A^3$, and $A^4$ are each independently P, As or N;
$E^2$ is independently C or N;
$E^3$ is independently C, Si, or Ge;
$E^4$ is independently C, Si, or Ge;
and $E^5$ is independently C, Si or Ge.
$M^1$, $M^2$, $M3$, and $M^4$ each is a metal atom independently selected from the group consisting of ruthenium, rhodium, palladium, osmium, iridium and platinum;

$Q^1$, $Q^2$, $Q^3$, and $Q^4$ are each independently a direct bond, —$CH_2$—, —$CH_2CH2$—, —CH=CH—;

in structure I, structure II or structure IV, $R^1$, $R^2$, $R^3$, and $R^4$ are each independently selected from alkyl, alkenyl, cycloalkyl, and aryl, or $R^1$ and $R^2$ together and $R^3$ and $R^4$ together form a ring structure having from 4 to 10 carbon atoms, or in structure III, $R^5$, $R^6$, $R^7$, and $R^8$ are each independently selected from alkyl, alkenyl, cycloalkyl, and aryl, or $R^5$ and $R^6$ together and $R^7$ and $R^8$ together form a ring structure having from 4 to 10 carbon atoms;

at a temperature of between about 100° and 250° C. for between about 1 hr and 300 days in the absence of $N_2$.

2. The improved process of claim 1, which further includes:

(b) recovering the alkene product, hydrogen or combinations thereof of step (a).

3. The improved process of claim 1 where the soluble complex is structure I.

4. The improved process of claim 1 wherein $M^1$ is Rh, Ir, or Ru.

5. The improved process of claim 1 wherein A is structure II.

6. The improved process of claim 1 wherein the stoichiometric ratio of alkyl-containing compound to complex of structure A is between about 200/1 and 10,000/1.

7. The process of claim 1 wherein:

A is structure II:

$A^1$ and $A^2$ are each P.

$M^1$ and $M^2$ are Rh, Ru, or Ir; and $R^1$, $R^2$, $R^3$, and $R^4$ are each t-butyl.

8. The process of claim 1 wherein:

A is structure II:

$A^1$ and $A^2$ are each P.

$M^1$ and $M^2$ are selected from Rh, Ru, and Ir;

$Q^1$ and $Q^2$ are each —$CH_2$—, and $R^1$, $R^2$, $R^3$, and $R^4$ are each t-butyl.

9. The process of claim 1 wherein:

the structure A is structure III;

$A^1$ and $A^2$ are each P;

$E^3$ and $E^4$ are carbon;

$M^3$ is selected from Rh, Ru, and Ir;

$Q^3$ and $Q^4$ are each —$CH_2$—, and $R^5$, $R^6$, $R^7$, and $R^8$ are each independently alkyl having 1 to 4 carbon atoms.

10. The process of claim 1 wherein the structure A is structure I.

$A^1$ and $A^2$ are each P.

$E^2$ is N, $M^1$ is selected from Ru and Ir, $Q^3$ and $Q^4$ are each —$CH_2$—, and the turnover is between about 1 and 5000.

11. An improved process to remove hydrogen from an allyl-containing compound having at least one

group to produce hydrogen and a corresponding compound having at least one

group, which process comprises:

(a) contacting the alkyl-containing compound from which $N_2$ has been removed with a soluble complex of structure A, which structure A is selected from structures I, II, III or IV;

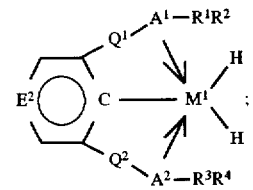 I

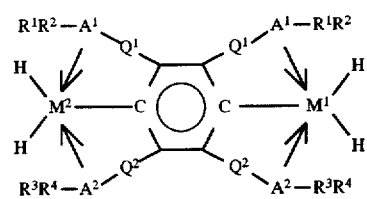 II

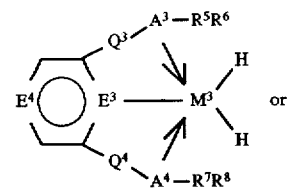 III or

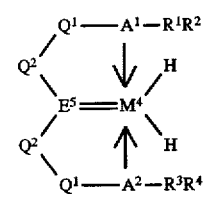 IV wherein:

$A^1$, $A^2$, $A^3$, and $A^4$ are each independently P, As or N;

$E^2$ is independently C or N;

$E^3$ is independently C, Si, or Ge;

$E^4$ is independently C, Si, or Ge;

and $E^5$ is independently C, Si or Ge;

$M^1$, $M^2$, $M^3$, and $M^4$ is a metal selected from group consisting of ruthenium, rhodium, palladium, osmium, iridium, and platinum;

$Q^1$, $Q^2$, $Q^3$, and $Q^4$ are each independently a direct bond, —$CH_2$—or —$CH_2CH_2$—;

in structure I and II, $R^1$, $R^2$, $R^3$, and $R^4$ are each independently alkyl, alkenyl, cycloalkyl, and aryl, or $R^1$ and $R^2$ together and $R^3$ and $R^4$ together form a ring structure having from 4 to 10 carbon atoms, or in structure III, $R^5$, $R^6$, $R^7$, and $R^8$ are each independently selected from alkyl, alkenyl, cycloalkyl, and aryl, or $R^5$ and $R^6$ together and $R^7$ and $R^8$ together form a ring structure having from 4 to 10 carbon atoms.

at a temperature of between about 100° and 250° C for between about 0.5 hour and 30 days in the absence of $N_2$.

12. The process of claim 11 wherein (b) the alkene compound, hydrogen or combinations thereof of step (a) is recovered.

13. The process of claim 11 wherein A is structure I.

14. The process of claim 13 wherein $M^1$ is selected from Rh, Ir, and Ru.

15. The process of claim 11 wherein the stoichiometric ratio of alkyl-containing compound to complex of structure A is between about 200/1 and 10,000/1.

16. The process of claim 11 wherein:

A is structure I;

$A^1$ and $A^2$ are each P, $M^1$ is selected from Rh, Ru, and Ir, $Q^1$ and $Q^2$ are each —$CH_2$—, and $R^1$, $R^2$, $R^3$, and $R^4$ are each t-butyl.

17. The process of claim 16 wherein the temperature is between about 150° and 200° C.

18. The process of claim 11 where

A is structure IV, $A^1$ and $A^2$ are each P, $E^5$ is C, $M^4$ is selected from Rh, Ru, and Ir, $Q^1$ and $Q^2$ are each —$CH_2$—, and $R^1$, $R^2$, $R^3$, and $R^4$ are each t-butyl or phenyl.

19. The process of claim 11 wherein within structure I the moiety

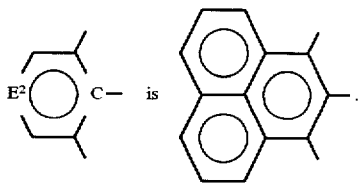

20. The process of claim 11 wherein the turnover is between about 100 and 4000.

* * * * *